Oct. 29, 1946. E. PRUSHEK Plant Pat. 714
CHRYSANTHEMUM PLANT
Filed Nov. 26, 1945
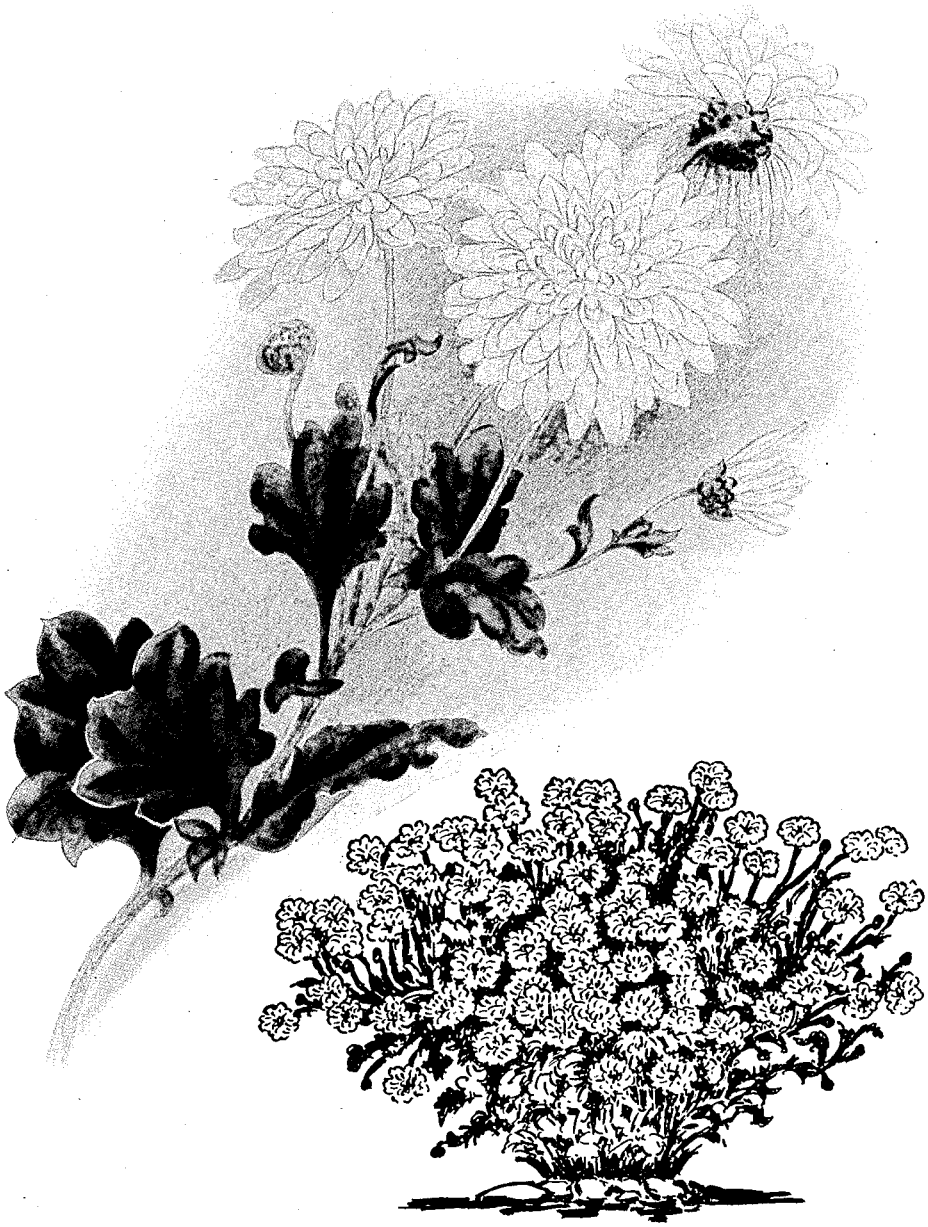
WITNESS
Addison E. Avery
INVENTOR,
EMIL PRUSHEK,
Rummler & Rummler & Davis,
Attorneys.

Patented Oct. 29, 1946

Plant Pat. 714

UNITED STATES PATENT OFFICE

714

CHRYSANTHEMUM PLANT

Emil Prushek, Berrien Springs, Mich., assignor to
C. J. Dunn, Benton Harbor, Mich.

Application November 26, 1945, Serial No. 630,750

1 Claim. (Cl. 47—60)

My present discovery relates to a new and distinct variety of *Chrysanthemum hortorum*, which was developed on my breeding plot in Berrien Springs, Michigan, through a succession of crosses that were hand-pollinated in planned directions since 1938, the seed parent being "Early Wonder" and the pollen parent is an unnamed seedling identified as C in the following genealogical chart:

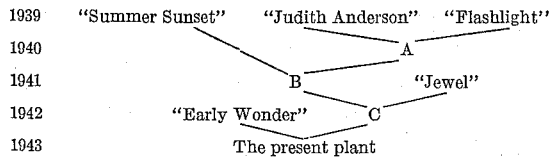

In the chart, the varieties identified as "Judith Anderson," "Flashlight" and "Jewel" are unpatented; "Summer Sunset" is the subject of Plant Patent No. 561; "Early Wonder" is the subject of Plant Patent No. 490; and those identified by A, B and C are unnamed seedlings.

The main object of this invention was to obtain a new chrysanthemum which would possess certain desired characteristics of the parent varieties and constitute a marked improvement in the progeny. These characteristics have been maintained by asexual propagation in quantity production by cuttings.

The distinctive features of this new variety are its early, long-season blooming habit through a succession of opening buds covering the older blooms; its lavish display of the rich, soft Mallow-Purple coloring of the flowers; the prolific quantity of blooms with heavy petalage and good lasting qualities; its freedom from disease, and its sturdy flower and leaf stalks. Its many-branched stalks are of adequate strength to support the profuse quantity of flowers.

The plant of this new variety is a cushion-type bush possessing decorative value in its dwarf habit of growth, its sturdy appearance, and its blossoms completely covering the bush. The foliage is healthy and attractive, is sufficient in quantity for such a floriferous variety, and has a decided resistance to wilt disease.

The plant does not break down, spread ungracefully or irregularly, but maintains a substantially upright position which is of great advantage both for commercial and decorative purposes. It has attained an average height of fifteen inches with a diameter of about twenty inches in its first year's growth from soft top cutting. In plant growth it has the usual characteristics of the species "hortorum."

The accompanying painting shows a stalk of the new chrysanthemum plant in its natural colors, with one flower fully developed and others at bud and intermediate stages and from points of view. A pen and ink sketch illustrates the plant growth.

The following is a detailed description of my new variety:

Parentage: Seedling.
- *Seed parent.*—"Early Wonder."
- *Pollen parent.*—Seedling C (a descendant of "Summer Sunset," "Judith Anderson," "Flashlight" and "Jewel").

Classification:
- *Botanical.*—*Chrysanthemum hortorum.*

*Flower*

Blooming habit: Recurrent—blooms early and profusely with long season through succession of opening buds and new blooms covering the older blooms.

Bud:
- *Size.*—Small.
- *Form.*—Round.
- *Color.*—Opening Mallow Purple.
- *Sepals.*—Number—about 25. Shape—short, pointed.
- *Calyx.*—Size—medium.

Bloom:
- *Size.*—2¼" diameter by 1" depth.
- *Form.*—Pompon.
- *Borne.*—Singly.
- *Stems.*—Substantial, medium length.
- *Petalage.*—Double, normally few stamens.
- *Color.*—Mallow Purple.
- *Discoloration.*—Not discolored by sun, rain or light frost.
- *Texture.*—Velvety, soft but substantial.
- *Affected by wet or hot weather.*—No.
- *Fragrance.*—Typical chrysanthemum odor.
- *Disease resistant.*—Yes, to wilt.
- *Lasting quality.*—On plant and as cut flower, both color and substance are very durable.

Genital organs: Completely hidden in the bloom and without distinguishing characteristics.
- *Stamens.*—Few.
- *Styles.*—Composite flower, one per each petal.
- *Stigma.*—Color, Yellow.

*Plant*

Form: Cushion-type bush.

*Growth.*—Vigorous, dwarf, branching, compact.

*Height.*—15 inches.

*Diameter.*—20 inches.

Foliage:

*Quantity.*—Sufficient for such a floriferous variety.

*Color.*—Hellebore Green.

*Size of leaf.*—2" x 2".

*Texture.*—Soft.

*Shape.*—Short, broad, lobed.

The color designations according to "A Dictionary of Color by Maerz and Paul" are as follows:

| | Part | Color | Plate | Letter | No. |
|---|---|---|---|---|---|
| Flower | Main body of lighter sections. | | 49 | A | 4 |
| | Shading into main color. | Mallow | 51 | I | 3 |
| | Shading into deepest tones. | | 51 | E | 7 |
| Stem | Top green stems (purple cast). | | 54 | C | 1 |
| | Shading into darker. | | 55 | E | 1 |
| Leaves | | Hellebore Green. | 23 | L | 3 |

A unique characteristic of this chrysanthemum is that it begins to flower unusually early in the latitude of Michigan. It is in full bloom by September 25 on the first-year plants grown from soft top cuttings. Propagation by sprouts or divisions and second-year plants give earlier bloom. From the time the buds and flowers appear, there is a continuous succession of buds and flowers until the end of the season. Thus there is a recurrent flowering period which begins two weeks earlier under the conditions prevalent in this region.

Large masses of blooms are produced on each plant at one time (the plant illustrated showed a count of 160 flowers in bloom). Thus there is a long season through a succession of opening buds covering the older blooms. The flowers maintain their distinctive coloring even when in their last stages and possess the quality of remaining fresh and natural in color for an exceedingly long time after being cut.

The compact central grouping of petals, which gives this chrysanthemum a dahlia-like appearance, remains solid until the bloom begins to dry and crumple. As the petals unfurl in the full bloom, the outer whorls decurve while the middle whorls retain their upstanding tubular position.

The only variety comparable to this new variety of chrysanthemum is "Lavender Lassie," an unpatented variety, but the two are distinctively different. The "Lavender Lassie" plant makes a more open, airy, lower growth with scattering bloom and its foliage and stems are more delicate. My new variety has a coarser, stiffer growth with blossoms covering the bush, and blooms two weeks earlier under conditions in my breeding plot. This new variety has wider petals, is of deeper color and its form and substance more nearly approach a greenhouse pompon. Its stems are heavier, longer and straighter, thus making a better cut-flower spray.

The velvety texture, distinctive mallow coloring, and unusual compactness of petals in the flower head, the sturdy stems, together with its superior keeping qualities, long blooming season and resistance to disease and weather combine to enhance the value of this plant as a commercial product. The plant is an ideal bush for border and group planting because of its profuse blooming, long season and compact dwarf shape.

I claim:

A new and distinct variety of chrysanthemum plant, characterized by its abundance of soft, Deep Mallow colored blossoms of pompon form; the uniformity and permanence of its color; its double, compact petalage; its long, sturdy flower and leaf stalks; its compact cushion-type of bush form; vigorous and hardy plant growth; its progressive succession of bush-covering blooms; and its resistance to disease and weather conditions, substantially as shown and described.

EMIL PRUSHEK.